United States Patent
Gleitsmann et al.

(10) Patent No.: US 12,156,952 B2
(45) Date of Patent: Dec. 3, 2024

(54) DEVICE AND METHOD FOR IRRADIATING A LIQUID

(71) Applicant: OSRAM GmbH, Munich (DE)

(72) Inventors: Tobias Gleitsmann, Michendorf (DE); Ulrich Hartwig, Berlin (DE)

(73) Assignee: OSRAM GMBH, Munich (DE)

( * ) Notice: Subject to any disclaimer, the term of this patent is extended or adjusted under 35 U.S.C. 154(b) by 368 days.

(21) Appl. No.: 17/584,138

(22) Filed: Jan. 25, 2022

(65) Prior Publication Data

US 2022/0305155 A1    Sep. 29, 2022

(30) Foreign Application Priority Data

Mar. 25, 2021   (DE) ............... 10 2021 202 957.4

(51) Int. Cl.
| | |
|---|---|
| *A61L 2/10* | (2006.01) |
| *A61L 2/20* | (2006.01) |
| *A61L 2/24* | (2006.01) |
| *A61L 2/26* | (2006.01) |

(52) U.S. Cl.
CPC ..................... *A61L 2/10* (2013.01); *A61L 2/20* (2013.01); *A61L 2/24* (2013.01); *A61L 2/26* (2013.01)

(58) Field of Classification Search
CPC ..... A61L 2/10; A61L 2/20; A61L 2/24; A61L 2/26; H05B 3/0052; B01D 53/007
See application file for complete search history.

(56) References Cited

U.S. PATENT DOCUMENTS

2006/0124556 A1* 6/2006 Fite .................... C02F 9/20
                                                              210/748.11

FOREIGN PATENT DOCUMENTS

| DE | 195 27 472 C1 | 3/1997 | |
|---|---|---|---|
| DE | 198 29 984 A1 | 1/2000 | |
| EP | 3105187 B1 * | 6/2017 | ............... A61L 2/10 |
| RU | 2541071 C2 * | 2/2015 | ............. C02F 1/325 |
| WO | 9911576 A1 | 3/1999 | |

* cited by examiner

*Primary Examiner* — David E Smith
*Assistant Examiner* — Hsien C Tsai
(74) *Attorney, Agent, or Firm* — ArentFox Schiff LLP

(57) ABSTRACT

The invention relates to a device for irradiating a liquid with electromagnetic radiation, in particular for sterilizing an in particular flowing liquid by means of UV radiation (UV reactor), comprising a container having an inlet for receiving the liquid and having an outlet for releasing the liquid from the container, wherein within the container a variable or adjustable irradiation zone is provided for irradiating the liquid with electromagnetic radiation, in particular UV radiation, emitted by a radiation source. In the irradiation zone the liquid is configured in the form of a liquid layer having the layer thickness which extends between the underside of the container and a gas bubble expanding above the liquid layer.

Figure 1:
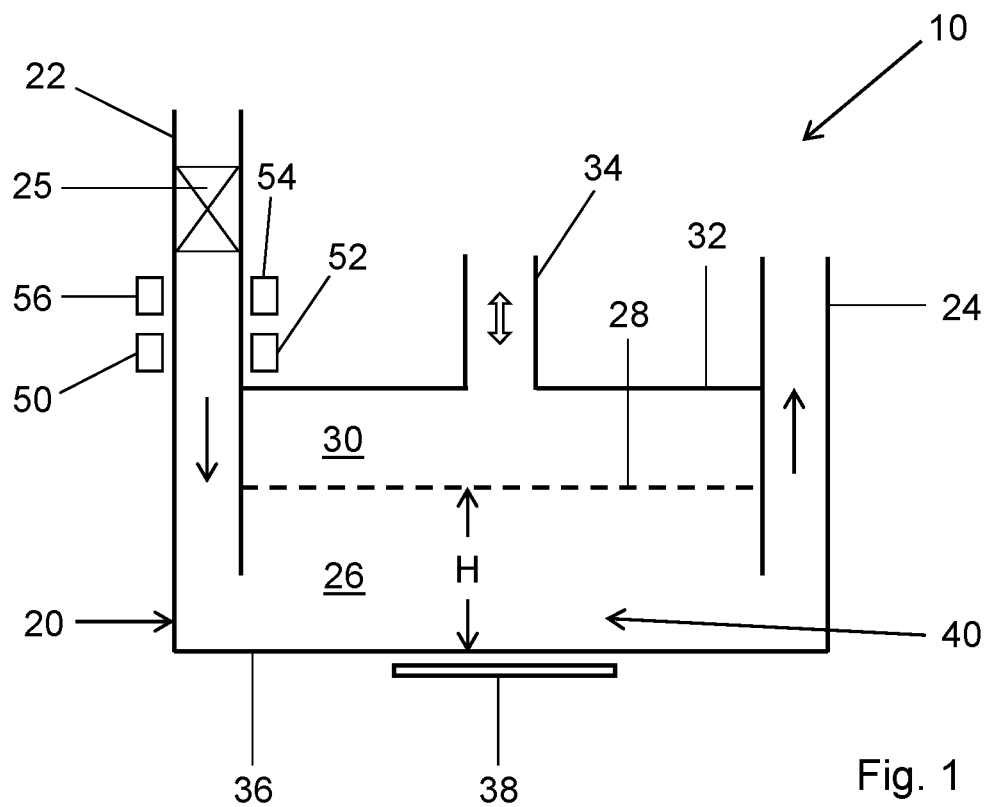

16 Claims, 4 Drawing Sheets

DEVICE AND METHOD FOR IRRADIATING A LIQUID

CROSS-REFERENCE TO RELATED APPLICATIONS

This application claims priority to, and the benefit of, German Application No. 10 2021 202 957.4, filed on Mar. 25, 2021, the contents of which are hereby incorporated by reference in their entireties.

The present invention relates to a device and a corresponding method for irradiating a liquid, in particular a flowing liquid, with electromagnetic radiation, in particular for sterilizing a liquid by means of ultraviolet radiation. The device comprises a container having an inlet for receiving the liquid and having an outlet, at which the liquid can be released from the container after flowing through the latter. Moreover, the device comprises a plurality of radiation sources, preferably LEDs, which are each designed for irradiating the liquid flowing in an interior of the container with electromagnetic radiation, in particular with wavelengths in the range of the UV radiation, preferably the UV-C radiation. Such devices are also referred to as UV reactors.

UV reactors can be used in diverse ways, for instance for treating drinking water or for sterilizing service water or process water used for example in industrial, agricultural or domestic applications (e.g. dishwashers, etc.). Liquids other than water, such as blood or milk for example, can also be sterilized by such UV reactors.

The radiation in the wavelength range of 200 nm to 280 nm proves to be particularly effective in this case, this radiation also being referred to as far UV or FUV radiation according to DIN 5031-7. This is accompanied by the adjacent range of 100 nm to 200 nm, which is correspondingly referred to as vacuum UV or VUV radiation.

In the present application, the wavelength ranges indicated above through to 280 nm are combined as UV-C radiation, those from 280 nm to 315 nm are combined as UV-B radiation and those from 315 nm to 380 nm are combined as UV-A radiation and used predominantly in UV reactors. For the purposes of this application, the range from 10 nm to 121 nm (extreme ultraviolet) is also covered by the term UV-C radiation used here.

For efficient sterilization, in this case, the radiation dose (Dose=intensity times time [Ws/m$^2$]) per unit volume of the liquid flowing through should be a constant. At the very least, however, the radiation dose per unit volume of the liquid flowing through must lie above a limit value that ensures sterilization of the respective unit volume in accordance with the requirements.

Liquid media having different optical properties, in particular scattering and absorption properties, e.g. on account of turbidities, have different penetration depths of electromagnetic radiation. If electromagnetic radiation is used to alter a property of the medium by means of radiation dosing, the geometry of the set-up, the power of the radiation source and the beam guidance must be correspondingly adapted to the optical properties of said medium.

In a turbid medium, the radiation intensity is greatly dependent on the distance with respect to the radiation source. In order to prevent the dose from decreasing too much at greater distances, it is thus necessary to vary the flow rate over the distance. Flow rates are difficult to monitor over a wide range within a reactor. Furthermore, very low flow rates increase the risk of sedimentation. In particular, a uniform dosing is difficult in the case of media in which the turbidity can vary over time.

The turbidity of a medium can be caused for example by scattering or absorbing particles. The latter can be of organic or inorganic origin. Examples would be dirt particles, microorganisms, algae or suspended particles, limescale particles or the like. Alternatively or additionally, turbidity can also be caused by emulsions or mixture with other liquids (e.g. with colloid constituents).

One example is a UVC reactor for sterilizing water. The sterilization performance of a UV reactor is linked to its germ reduction factor RF=lg(N(t)/N$_0$), where N$_0$ is the initial number of germs and N(t) is the reduced number of germs after a time t. The germ reduction follows the following dependence in a wide range in a simplified manner: N(t)=N$_0$·exp(−kD(t)), where D is the dose and k is a germ- and environment-specific constant.

The efficiency of UV reactors for sterilizing liquids is influenced by the penetration depth of the radiation into the liquid volume. Particularly in the case of UV-C radiation and turbid media, after just a few millimeters the incident light intensity has fallen to a few percent as a result of absorption and/or scattering, such that it is no longer possible to achieve a relevant disinfection effect for irradiated layer thicknesses of a few cm or more or a very high initial optical power would have to be used in order still to obtain a sufficient effect after the attenuation. In order to secure a sufficient disinfection effect, in practice disinfection systems are often approved only for a maximum UV transmission (see DVGW W 294-1:2006-06).

Ensuring the condition of a constant dose over the entire volume therefore necessitates particular precautions. Particularly if the penetration depth of the radiation varies over the course of time.

By suitably increasing the radiation power beyond a critical threshold value, for example by more than a factor of 10$^4$, a sufficient radiation power for reducing the reproductive germs can be attained in principle in all regions of the liquid that are to be disinfected.

Conventional UV reactors generally contain enough UVC radiation so that a sufficient dose is always obtained even in the case of varying turbidity. UVC lamp sources, in particular gas discharge lamps, have been used for this purpose in the past. A severe overdosing of the required radiation is possible here since the costs of the sources per watt of radiation power are low and the radiation sources are able in principle to emit large amounts of radiation (hundreds to thousands of watts depending on the type of lamp). In the simplest case, for the design of the sterilization system the "worst case" (most turbid possible liquid) can be assumed and the reactor and the radiation source can be designed in regard to this case. However, this solution approach results in a great reduction of the energy efficiency of the system on account of UV overdosings in a large portion of the irradiated region. This strategy is not economically viable in the case of semiconductor UVC sources (e.g. LEDs), on account of the significantly small maximum amounts of UV radiation and the high costs of present UV LEDs, in particular UV-C LEDs. Moreover, such a procedure would result in energy being wasted in the cases in which the turbidity of the medium is comparatively low.

It is therefore an object of the invention to develop a device of the generic type for irradiating a flowing liquid with electromagnetic radiation, in particular UV radiation, in such a way that the disadvantages mentioned above are overcome. In particular, the radiation effect, in particular also sterilization effect, is intended to be ensured as efficiency as possible even in the case of changing penetration depth, for example on account of changing scattering and absorption properties of the liquid to be irradiated or sterilized.

The object is achieved by means of a device for irradiating, in particular also for sterilizing, a flowing liquid having the features of patent claim 1. Advantageous developments of the device according to the invention and configurations of the invention are the subject matter of the dependent claims, of the description and of the figures.

The starting point is a device for irradiating/sterilizing a flowing liquid by means of UV radiation which comprises a container having an inlet for receiving the liquid and having an outlet, at which the liquid can be released from the container after flowing through the latter. In essence, therefore, a flow reactor is involved here. Nevertheless, the invention includes a liquid which is situated in the container and which is admitted beforehand, irradiated/sterilized by means of UV radiation and discharged later.

Within the container, an irradiation zone is provided for the liquid to be irradiated, wherein the electromagnetic radiation can be radiated into said irradiation zone from the bottom, i.e. the underside of the container. Moreover, a gas bubble is provided above the liquid level. The term "gas" or "gas bubble" here in a generalizing way is intended to encompass both a single gas and an arbitrary mixture of different gases, e.g. in particular also air, or an air bubble. The liquid level constitutes an interface between the liquid in the container and the gas bubble and, on account of the difference in refractive index of the two media, functions as a reflector for the radiation radiated in from the underside of the container and thus contributes to an increase in efficiency. Via a gas feed, which is preferably arranged on the top side of the container, it is possible to adjust the gas pressure and thus the expansion of the gas bubble within the container and ultimately also the liquid cross-section or the layer thickness, or respectively the depth of the liquid in the irradiation zone.

This makes it possible to ensure that over the entire irradiation zone of the reactor, a certain minimum amount of radiation penetrates through the liquid layers adapted in the depth thereof to the respective liquid property, for example turbidity. As the turbidity of the liquid increases, for example, the gas pressure is increased in order that the gas bubble expands more and the remaining depth for the liquid thus correspondingly decreases until an equilibrium is established. Conversely, the gas pressure can be decreased again as soon as the turbidity decreases, as a result of which the gas bubble likewise decreases and the liquid depth thus increases until an equilibrium is established again.

In one advantageous development of the device according to the invention, a sensor-based closed-loop control circuit is provided, in the case of which the layer thickness through which radiation is transmitted is adjusted depending on the UV transmissivity of the medium through which radiation is transmitted, e.g. depending on a sensor signal of the light being transmitted, for example from one or more photodiodes.

A closed-loop control can be effected for example by the pressure of a gas supply (gas ballast) connected to the gas bubble being varied depending on the sensor signal. The requisite change in the gas pressure can be effected e.g. thermally, by means of a pump or by volume compression ("balloon principle"). In this case, the closed-loop control is designed such that for example with a turbidity-dictated decrease in the photodiode signal, the gas bubble expands and thereby reduces the liquid cross-section or the liquid depth.

A closed-loop control can for example also be designed such that with increasing turbidity, the volumetric flow rate in the reactor is reduced, e.g. with the aid of a controllable valve. The internal pressure of the container or of the inlet and outlet pipes decreases as a result. Thus, the gas bubble can expand and the layer thickness of the liquid flowing through the irradiation zone decreases to an equilibrium value.

The turbidity of the medium can be measured in the admission region (inlet) and/or discharge region (outlet). By way of example, additional secondary radiation sources (auxiliary or measurement radiation sources) can be used for this purpose. In this case, one or more wavelengths can be used in order to address different absorption and scattering properties of the medium in a targeted manner.

The sensors, for example photodiodes, can measure the directly transmitted portion, the forward-scattered portion and the backward-scattered portion of the auxiliary radiation and thus partly distinguish between absorbed and scattered portions of the radiation.

Both the radiation sources (primary and secondary) and the sensors can be equipped with optical components, e.g. lenses, TIR lenses (Total Internal Reflection), CPCs (Compound Parabolic Concentrator), stops, reflectors, lens plates and/or optical diffusors.

The control signal can also be ascertained without auxiliary radiation, but rather with the aid of the primary radiation. To that end, the sensors (e.g. photodiodes) are arranged on or in the reactor container directly. In this case, the radiation of the primary radiation source can be used to determine the optical properties of the medium. However, it should be taken into account here that the optical properties of the reactor chamber also vary with the position of the boundary layer. Therefore, the position of the boundary layer is ascertained, e.g. acoustically by means of ultrasonic waves. The optimum new position of the boundary layer can be ascertained from the position of the boundary layer and the photodiode signals. The photodiode signals and the instantaneous position of the boundary layer thus influence the closed-loop control of the gas pressure. In this case, the functional relationship is greatly dependent on the reactor geometry and accordingly has to be determined individually for each reactor design.

Furthermore, a closed-loop control of the size of the gas bubble and thus of the layer thickness of the liquid can also be effected depending on the lifetime behavior of the radiation source, for example of UVC LEDs. As a result, the influence of a decrease—occurring over the course of time—in the radiation power of the radiation source on the sterilization of the liquid can be compensated for or at least reduced.

Since the irradiation intensity in the reactor decreases with the distance with respect to the UV radiation source, it is desirable to be able to adjust the flow of the medium in the irradiation zone over the depth in order to attain a uniform dosing of the radiation over the volume.

One embodiment provides V-shaped constrictions of the reactor or other shapes of baffle plates or guide plates that project into the reactor vessel from above. A movable perforated plate with varying hole sizes is also possible. The baffle plates or guide plates are adjusted depending on position of the boundary layer. Since the irradiance is the highest near the source and decreases with distance, the baffle plate reduces the volumetric flow rate with increasing distance, such that the dose, the product of irradiance and irradiation duration, is independent of the distance with respect to the source.

In order to increase the efficiency of the reactor by optimizing the interface reflectivity, objects which float on the surface of the liquid and reflect or diffusively backscatter radiation, e.g. spheres or balls, can be introduced. A floating film is likewise possible.

The boundary layer can also be excited by acoustic waves. The boundary layer can thus reflect radiation like a reflector by means of total internal reflection as a result of the change in refractive index between the liquid and the gas. With a plurality of actuators, this excitation can also produce 2-dimensional patterns on the surface of the liquid. It is particularly advantageous to generate the waves in the shape of 4-sided or 6-sided pyramids. For this purpose, it is also necessary to effect excitation with higher harmonic frequencies according to the Fourier series.

Moreover, it is possible to allow a thin liquid film having a different refractive index than the primary medium to float on the latter and thus to realize a Bragg mirror. Constructive interference of the waves from the different surfaces enables a wavelength-sensitive reflective layer to be realized. It is thus possible to distinguish between measurement wavelength and effective wavelength. In this case, the optical path length through the respective layers, formed from the product of refractive index and geometric thickness of the layer, must be one quarter of the effective wavelength.

The medium can also be irradiated from the gas bubble side. One advantage of such an arrangement is that contamination, e.g. the formation of a biofilm, or limescale deposits, on the boundary layer cannot take place.

In addition to the air bubble volume, the flow rate (volumetric flow rate), the baffle plates and the source current can also be controlled by means of the sensor signals.

As an alternative or in addition to air, the bubble can be filled with further gases having for example an additional sterilization effect, e.g. $O_3$, $Cl_2$, $ClO_2$, $H_2O_2$.

Moreover, the upper surface of the vessel, in the region of the gas bubble, can be provided with a photocatalytically active coating in order to interact with the UV radiation that has penetrated through the boundary layer between liquid and air (radiation recycling). Said coating can be embodied for example such that it:
reflects or diffusely scatters the impinging radiation and thus achieves a shielding effect toward the outside,
generates an additional sterilization effect by means of absorption in a photocatalytically active material, e.g. $TiO_2$, $ZnO$, e.g. photocatalytic oxidation (PCO).

Provision can also be made for the gas bubble to temporarily occupy the entire reactor space. This draining of the reactor space enables biofilms to be compensated in a targeted manner in the case of sterilization reactors.

Further advantages, features and details of the invention are evident from the following description of preferred embodiments, and with reference to the drawings. In this case, features that are identical or of identical type may also be designated by identical reference signs hereinafter, for the sake of simplicity.

Figure 2:
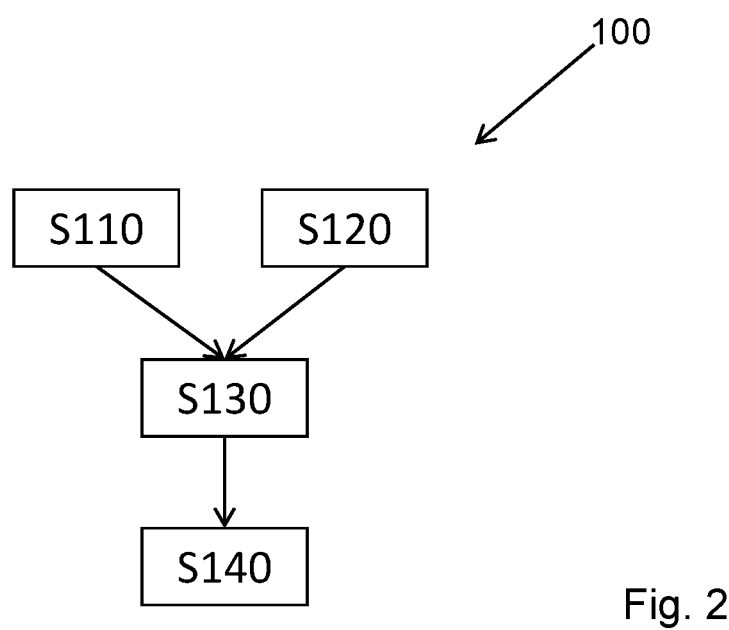
Figure 3:
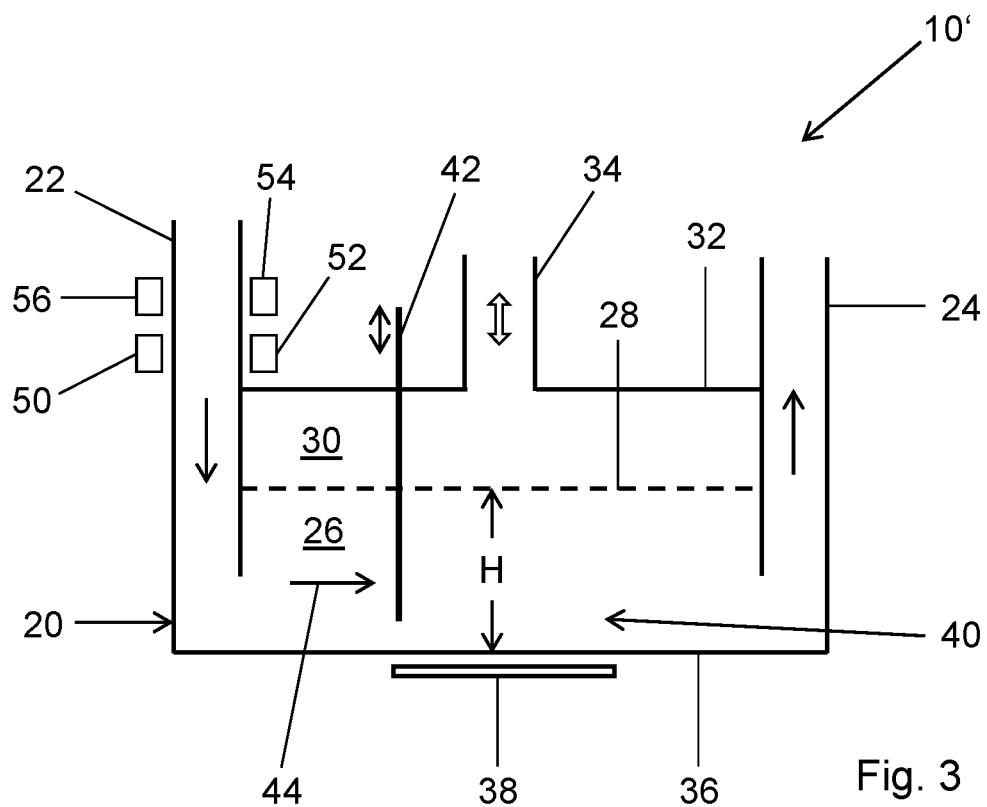
Figure 4:
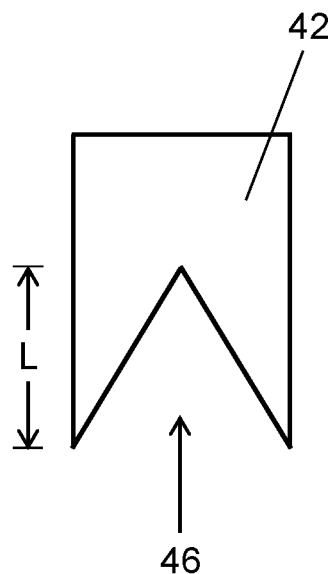
Figure 5:
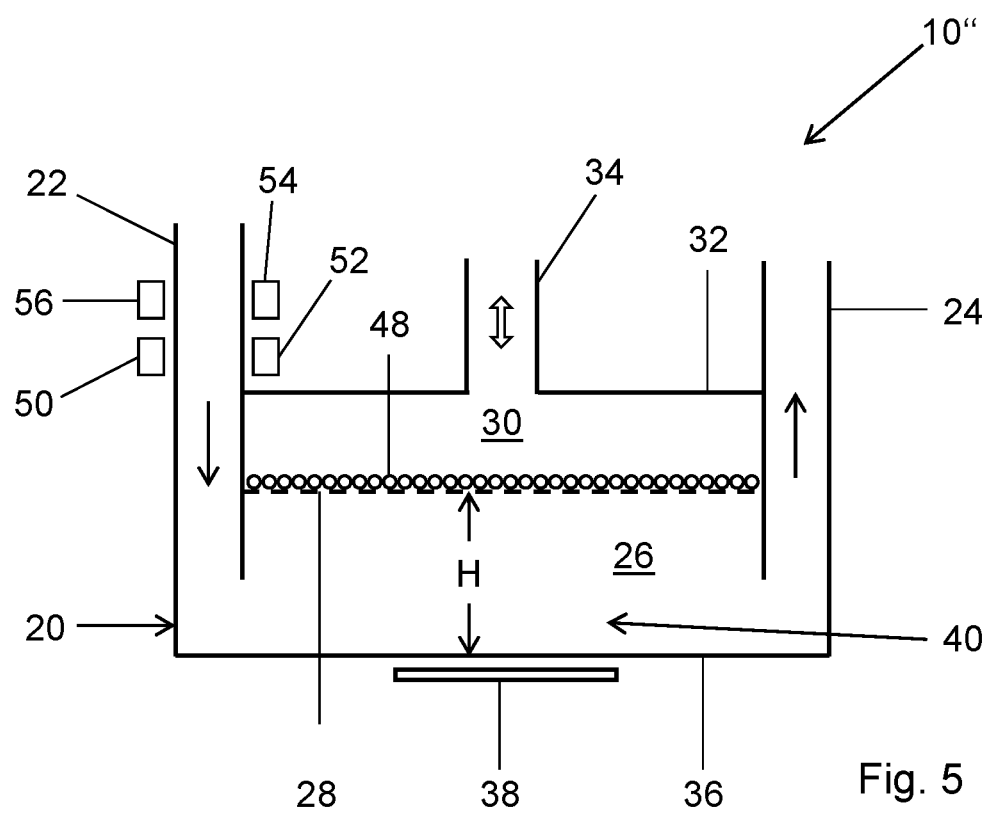
Figure 6:
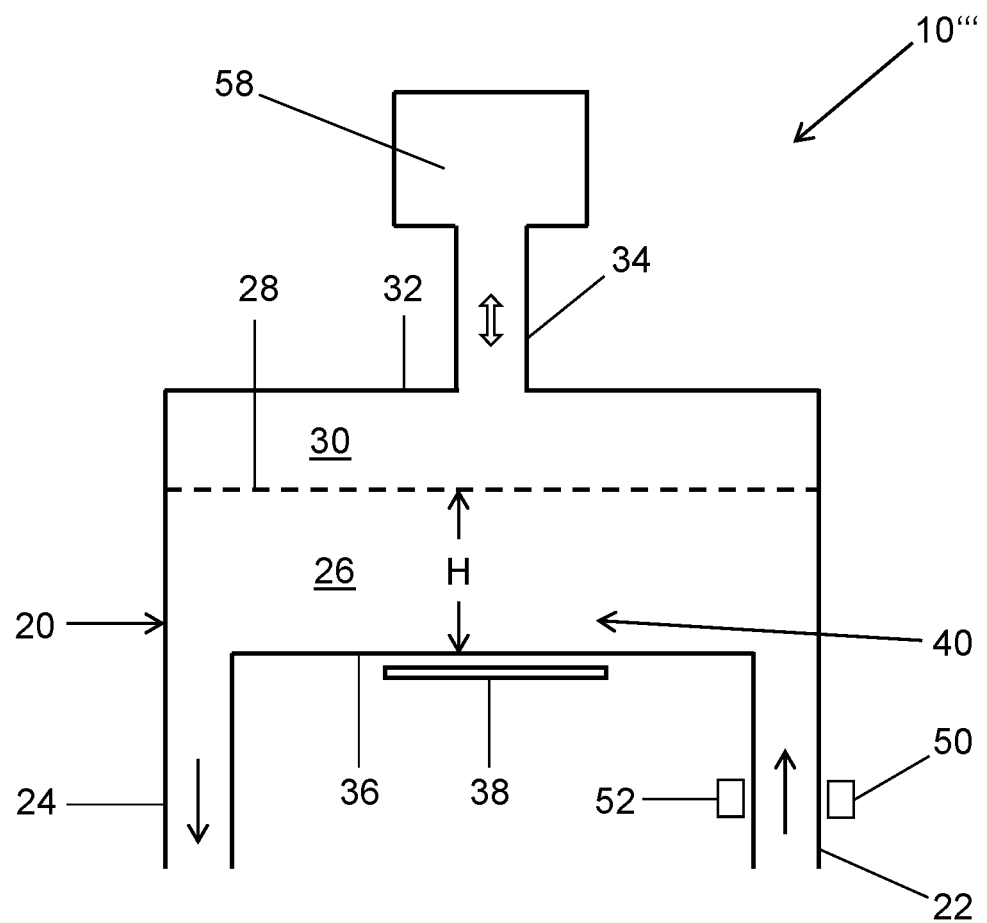

In the figures here:
FIG. 1 shows a schematic illustration of a UV reactor with a gas bubble according to the present invention;
FIG. 2 shows a schematic flow diagram for an embodiment of the closed-loop control of the layer thickness of the liquid in the UV reactor;
FIG. 3 shows a schematic illustration of a UV reactor with baffle plate according to the present invention;
FIG. 4 shows a schematic illustration of a baffle plate for a UV reactor according to the present invention;
FIG. 5 shows a schematic illustration of a UV reactor with reflective balls floating on the surface of the liquid according to the present invention;
FIG. 6 shows a schematic illustration of a UV reactor with changed inlet and outlet by comparison with FIG. 1.

FIG. 1 shows a schematic illustration of a simplified sectional view of one exemplary embodiment of the invention. The illustration shows a UV reactor 10 comprising a container 20 and an inlet pipe 22 and an outlet pipe 24 for a liquid 26 to be sterilized. The liquid 26 flowing in and out is symbolized by corresponding arrows. Instead of being arranged as illustrated in FIG. 1, inlet and outlet pipes can alternatively also be arranged differently, for example at the underside of the container (not illustrated). The liquid 26 typically only fills part of the container 20, namely up to the liquid level 28. The height H of the liquid level 28 is adjusted by way of a gas bubble 30. For this purpose, gas is admitted into the container 20 via a gas feed 34 arranged on the top side 32 of the container 26. The expansion of the gas bubble 30 and thus the height H of the liquid level 28 can be adjusted by the gas pressure being varied (indicated by the wide double-headed arrow).

Alternatively or additionally, the height H of the liquid level can also be adjusted by the volumetric flow rate of the liquid 26 being changed. For this purpose, a control valve 25 is provided in the inlet pipe 22. Reducing the volumetric flow rate also reduces the liquid pressure in the inlet pipe 22 and thus in the container 20. As a result, the gas bubble 30 can expand more even with constant gas pressure and the height H of the liquid level 28 is reduced.

Arranged at the underside 36 of the container 26 is a radiation source 38, which extends at least over part of the underside 36, preferably a plurality of UV-C LEDs, for example of the OSLON UV 3636 type from OSRAM Opto Semiconductors. During operation, the radiation source 38 irradiates the liquid 26 within an irradiation zone 40 through the radiation-transmissive underside 36 of the container 26. In this way, therefore, adjusting the height H of the liquid level ultimately adjusts the layer thickness of the liquid 26 to be irradiated in the irradiation zone 40, depending on the degree of turbidity of the liquid 26. Alternatively, the radiation source 38 can also be arranged such that the liquid is irradiated from the side of the gas bubble, for example by the radiation source being arranged on the top side of the container or else within the container (not illustrated).

Optionally, a sensor-based closed-loop control circuit is provided (not illustrated), which independently adjusts and as necessary readjusts the adjustment of a suitable layer thickness or respectively the height H of the liquid level 28 depending on the measured UV transmissivity of the liquid 26. For this purpose, in the region of the inlet pipe 22, there are arranged a secondary UV radiation source 50 and three assigned radiation sensors 52, 54, 56 for the measurement of the direct, scattered and backscattered UV radiation, respectively. On the basis of the measurement signals of the radiation sensors 52, 54, 56, the gas pressure in the gas bubble 30 is controlled with the aid of a controllable gas supply or gas ballast (not illustrated).

Alternatively, in the region of the outlet pipe 24, too, a corresponding measurement of the UV transmissivity of the outflowing liquid 26 can be provided (not illustrated).

In a further alternative embodiment, the radiation sensors are arranged (not illustrated) in the region of the top side 32

(for the measurement of the direct and scattered radiation) and underside 36 (for the measurement of the backscattered radiation). In this case, the radiation of the primary radiation source 38 can be used to determine the UV transmissivity of the liquid 26. However, the position of the liquid level 28 should also be taken into account here, i.e. the position of the optical boundary layer between liquid 26 and gas 39, since that affects the optical properties of the reactor chamber 10. The position of the boundary layer 28 can be determined by means of ultrasonic waves, for example. For this embodiment, FIG. 2 illustrates a rough flow diagram 100 for the closed-loop control of the layer thickness H in the case of changes in the degree of turbidity of the liquid. Both the measurement signals of the radiation sensors (step S110) and the ascertained position of the boundary layer (step S120) influence the determination of the new position of the boundary layer 28 (step S130). In the next step S140, the gas pressure required for the new position of the boundary layer 28 is ascertained. In the case where the degree of turbidity is measured by means of an additional secondary UV radiation source 50 as illustrated in FIG. 1, step S120 is omitted.

FIG. 3 shows a schematic illustration of a simplified sectional view of a further exemplary embodiment of the invention. The UV reactor 10' has a baffle plate 42, which dips into the liquid 26 approximately perpendicular to the liquid level 28 or to the main flow direction 44. The dipping depth is variable (indicated by the thin double-headed arrow). The baffle plate 42 serves for adjusting the flow of the liquid 26 at different depths in order to obtain as far as possible a uniform dosing of the radiation over the liquid volume in the irradiation zone 40.

FIG. 4 shows a schematic illustration of the baffle plate 42 in a plan view in the main flow direction 44. The baffle plate 42 has a rectangular basic shape with a V-shaped cutout 46 of length L, which cutout opens in the dipping direction. With the aid of this V-shaped cutout 46, it is possible to influence the flow profile of the liquid 26 in the region of the irradiation zone 40 such that the flow decreases with the distance from the radiation source 38, or conversely the flow increases with the depth with respect to the liquid level 28. It is thereby possible to improve the uniformity of the dosing of the radiation at different depths. Preferably, the length L of the cutout 46 is dimensioned such that it extends as far as the maximally envisaged height H of the liquid level 28, in order to ensure a suitable adjustment of the flow. An alternative embodiment for a baffle plate provides a perforated plate, in which the hole size preferably decreases in the direction of the liquid level (not illustrated). A plurality of baffle plates are also possible, e.g. one in front of and one behind the gas bubble, in order to control the flow over a wider region.

FIG. 5 shows a schematic illustration of a simplified sectional view of a further exemplary embodiment of the invention. The UV reactor 10" has a multiplicity of reflective or at least diffusively backscattering balls or spheres 48 floating on the liquid level 28. At least part of the radiation which comes from the radiation source 38 and remains after traversing the liquid layer and which is not reflected by the interface between the liquid 26 and the gas of the gas bubble 30, but rather is transmitted thereby, is reflected by the balls 48 likewise back into the liquid 26. The efficiency of the UV reactor 10" is increased as a result.

FIG. 6 shows a schematic illustration of a simplified sectional view of a further exemplary embodiment of the invention. In the case of this UV reactor 10''', the inlet pipe 22 and the outlet pipe 24 are arranged at the underside 36 of the container 20. A gas supply container 58 is additionally provided, which is connected to the gas feed 34 at the top side 32 of the container 20 and thus to the gas bubble 30. By heating or cooling the gas supply in the container 58, it is possible to increase or reduce the gas pressure and thus to increase or decrease the expansion of the gas bubble 30. For this purpose, the gas supply container is equipped with a heating and cooling device (not illustrated). Alternatively, the pressure can also be increased by means of compression, for example by a gas compressor being connected to the gas feed or the gas supply container being of compressible design in the manner of bellows (not illustrated).

The invention relates to a device for irradiating a liquid with electromagnetic radiation, in particular for sterilizing an in particular flowing liquid by means of UV radiation (UV reactor), comprising a container having an inlet for receiving the liquid and having an outlet for releasing the liquid from the container, wherein within the container a variable or adjustable irradiation zone is provided for irradiating the liquid with electromagnetic radiation, in particular UV radiation, emitted by a radiation source. In the irradiation zone the liquid is configured in the form of a liquid layer having the layer thickness H which extends between the underside of the container and a gas bubble expanding above the liquid layer. By adapting the expansion of the gas bubble within the container, for example by changing the gas pressure, and as a result thereof the layer thickness H of the liquid in the irradiation zone, efficient operation of the (UV) reactor is achieved for different degrees of turbidity of the liquid. Optionally, the penetration depth of the radiation is detected by a sensor and the layer thickness H is adjusted appropriately on the basis of the sensor signal.

LIST OF REFERENCE SIGNS 10, 10', 10", 10''' UV reactor
20 Container
22 Inlet pipe
24 Outlet pipe
25 Control valve
26 Liquid
28 Liquid level
30 Gas bubble
32 Top side of the container
34 Gas feed
36 Underside of the container
38 Radiation source
40 Irradiation zone
42 Baffle plate
44 Main flow direction
46 V-shaped cutout
48 Ball/sphere
50 Secondary radiation source
52 Radiation sensor
54 Radiation sensor
56 Radiation sensor
58 Gas supply container
H Height of the liquid level/layer thickness
L Length of the V-shaped cutout

The invention claimed is:
1. A device for irradiating a liquid, in particular a flowing liquid, with electromagnetic radiation, in particular for sterilizing a liquid by means of UV radiation (UV reactor), comprising:

a container having an inlet for receiving the liquid and having an outlet for releasing the liquid from the container, wherein an irradiation zone for irradiating the liquid is provided within the container, and at least one radiation source configured to emit electromagnetic radiation, in particular light having wavelengths in the range of the UV radiation into the irradiation zone, wherein the device is designed to the effect that a gas bubble is producible within the container and above the liquid level of the liquid situated in the container in order thereby to adjust the layer thickness of the liquid in the irradiation zone.

2. The device as claimed in claim 1, comprising an adjustable gas feed for adjusting the expansion of the gas bubble within the container and thus the resulting layer thickness of the liquid.

3. The device as claimed in claim 2, wherein the gas feed is arranged at the top side of the container.

4. The device as claimed in claim 2, wherein the expansion of the gas bubble is adjusted on the basis of the gas pressure of a gas supply connected to the gas feed.

5. The device as claimed in claim 1, comprising a sensor designed for measuring a property of the liquid, in particular the degree of turbidity.

6. The device as claimed in claim 5, comprising a measurement radiation source designed and arranged to emit the measurement radiation for the sensor.

7. The device as claimed in claim 1, comprising a closed-loop control circuit designed to control the adjustment of the expansion of the gas bubble within the container depending on the measurement signal of the sensor.

8. The device as claimed in claim 1, comprising one or more radiation-reflecting objects floating on the liquid level, for example a floating film or floating balls.

9. The device as claimed in claim 1, wherein the inside of the container at least in the region of the gas bubble, is provided with a coating that reflects the radiation or that comprises a photocatalytic material having a sterilizing effect.

10. The device as claimed in claim 1, wherein the gas bubble contains air.

11. The device as claimed in claim 1, wherein the gas bubble contains gases having a sterilizing effect.

12. A method for irradiating a liquid with electromagnetic radiation, in particular for sterilizing a liquid comprising:

providing a device as claimed in claim 1;

connecting the inlet of the device to a source of the liquid and the at least one radiation source to an electrical energy supply source;

passing the liquid through the inlet into the container;

feeding the gas into the container through the gas feed; and adjusting the expansion of the gas bubble within the container and thus the resulting layer thickness of the liquid in the irradiation zone in accordance with at least one property, for example the degree of turbidity, of the liquid.

13. The method as claimed in claim 12, wherein adjusting the expansion of the gas bubble is effected by one or more of the following:

adjusting the gas pressure of the gas bubble;

adjusting the volumetric flow rate of the liquid.

14. The method as claimed in claim 12, additionally comprising:

measuring at least one property, including the degree of turbidity, of the liquid with the aid of the sensor and using the measurement signal of the sensor for adapting the expansion of the gas bubble to a change in the measurement signal.

15. The method as claimed in claim 12, additionally comprising:

returning the liquid to the source or transferring the liquid into some other reservoir via the outlet.

16. The method as claimed in claim 12, additionally comprising:

expanding the gas bubble such that the gas bubble occupies the entire space in the container for a time duration.

* * * * *